United States Patent
Choi et al.

(10) Patent No.: US 11,241,373 B2
(45) Date of Patent: Feb. 8, 2022

(54) COSMETIC COMPOSITION OF DISPERSION FORMULATION COMPRISING SPHERICAL PARTICLE

(71) Applicant: Amorepacific Corporation, Seoul (KR)

(72) Inventors: Soojeong Choi, Yongin-si (KR); Sungil Park, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 46 days.

(21) Appl. No.: 16/635,250

(22) PCT Filed: Jul. 31, 2018

(86) PCT No.: PCT/KR2018/008690
§ 371 (c)(1),
(2) Date: Jan. 30, 2020

(87) PCT Pub. No.: WO2019/027230
PCT Pub. Date: Feb. 7, 2019

(65) Prior Publication Data
US 2020/0214954 A1 Jul. 9, 2020

(30) Foreign Application Priority Data
Jul. 31, 2017 (KR) .................. 10-2017-0096881

(51) Int. Cl.
| A61K 8/34 | (2006.01) |
|---|---|
| A61K 8/02 | (2006.01) |
| A61K 8/04 | (2006.01) |
| A61K 8/60 | (2006.01) |
| A61K 8/68 | (2006.01) |
| A61K 8/92 | (2006.01) |
| A61K 8/97 | (2017.01) |
| A61Q 19/08 | (2006.01) |

(52) U.S. Cl.
CPC ............ *A61K 8/345* (2013.01); *A61K 8/025* (2013.01); *A61K 8/04* (2013.01); *A61K 8/60* (2013.01); *A61K 8/68* (2013.01); *A61K 8/92* (2013.01); *A61K 8/97* (2013.01); *A61Q 19/08* (2013.01); *A61K 2800/41* (2013.01); *A61K 2800/48* (2013.01)

(58) Field of Classification Search
CPC . A61K 8/345; A61K 8/97; A61K 8/92; A61K 8/68; A61K 8/025; A61K 8/04; A61K 8/60; A61K 2800/48; A61K 2800/41; A61K 8/342; A61K 8/34; A61K 8/9789; A61K 2800/596; A61Q 19/08; A61Q 19/02; A61Q 19/00
See application file for complete search history.

(56) References Cited

U.S. PATENT DOCUMENTS

| 6,783,766 | B2 | 8/2004 | Pate et al. | |
|---|---|---|---|---|
| 9,084,818 | B2 | 7/2015 | Barathur et al. | |
| 9,662,282 | B2 * | 5/2017 | Jiang | A61K 8/11 |
| 9,949,900 | B2 | 4/2018 | Lee et al. | |
| 2010/0190740 | A1 | 7/2010 | L'Alloret et al. | |
| 2010/0233105 | A1 | 9/2010 | Shinagawa | |
| 2012/0114573 | A1 * | 5/2012 | Amalric | A61K 8/35 424/59 |
| 2014/0220139 | A1 | 8/2014 | Park et al. | |
| 2016/0199269 | A1 | 7/2016 | Lee et al. | |

FOREIGN PATENT DOCUMENTS

| EP | 1702674 A1 * | 9/2006 | ............ B01J 13/20 |
|---|---|---|---|
| KR | 10-0311200 B1 | 2/2002 | |
| KR | 10-2010-0071013 A | 6/2010 | |
| KR | 10-2010-0105323 A | 9/2010 | |
| KR | 10-2013-0030093 A | 3/2013 | |
| KR | 10-2013-0055069 A | 5/2013 | |
| KR | 10-2015-0022434 A | 3/2015 | |
| KR | 10-1579063 B1 | 12/2015 | |
| KR | 10-2017-0003163 A | 1/2017 | |
| WO | 2011/116963 A2 | 9/2011 | |
| WO | 2016/046211 A1 | 3/2016 | |

OTHER PUBLICATIONS

International Search Report for PCT/KR2018/008690 dated Feb. 8, 2019 [PCT/ISA/210].
European Patent Office, Extended European Search Report dated Mar. 29, 2021, issued in Application No. 18840502.1.

* cited by examiner

*Primary Examiner* — Quanglong N Truong
(74) *Attorney, Agent, or Firm* — Sughrue Mion, PLLC

(57) ABSTRACT

The present disclosure relates to a cosmetic composition of dispersion formulation including: a aqueous phase as an external phase; and an oil phase consisting of spherical particles dispersed in the aqueous phase, wherein the spherical particles including an alcohol having 22 or less carbon atoms and a sucrose-based surfactant, wherein the cosmetic composition has excellent formulation stability by including the spherical particles, and causes no irritation when applied to the skin.

12 Claims, 9 Drawing Sheets

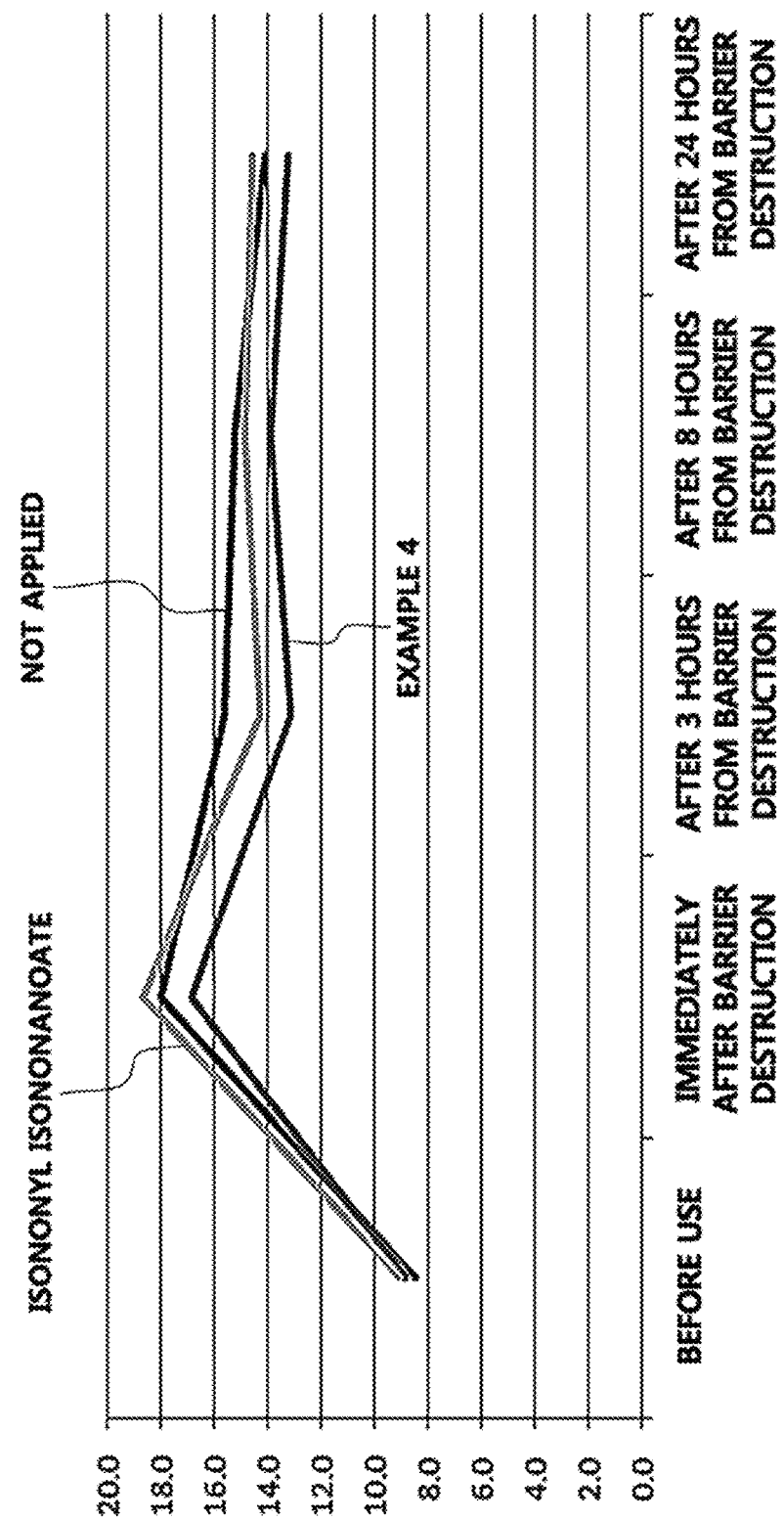

COSMETIC COMPOSITION OF DISPERSION FORMULATION COMPRISING SPHERICAL PARTICLE

CROSS-REFERENCE TO RELATED APPLICATION

This application is a National Stage of International Application No. PCT/KR2018/008690 filed Jul. 31, 2018, claiming priority based on Korean Patent Application No. 10-2017-0096881, filed on Jul. 31, 2017, and all the benefits accruing therefrom under 35 U.S.C. § 119 and the contents of which in its entirety are herein incorporated by reference.

TECHNICAL FIELD

Disclosed is a cosmetic composition of dispersion formulation which comprises spherical particles and exhibits excellent dispersibility of the spherical particles in the composition and excellent stability of formulation.

BACKGROUND ART

Cosmetics are used as a means to protect the skin from the external environment and to recover and maintain the skin. In addition, cosmetics have a function of replenishing the moisture and oil of skin lost by daily washing and of delaying skin aging.

Recent developments of cosmetics are characterized by a big trend in which a unique appearance different from the existing one or differentiated feel of use is imparted to cosmetics or the development and introduction of ingredients of which the effects are immediately revealed as soon as the ingredients are applied to the skin.

In particular, a number of solid capsuled dispersion skin, essence and cream formulations which are visually differentiated and attract attention of consumers have been developed. The solid capsuled raw materials are mostly in bead forms containing agar or cellulose, and the formulations are prepared through the post-injection from the outside and dispersion in the manufacturing process.

However, the solid capsuled bead raw materials lack flexibility and are hard, and the beads are often not melted or broken when being applied to the skin to often cause irritation. In the case of amorphous solid lipid particle dispersion formulations, there is a problem that the ununiformity of the formulations decreases the aesthetic value or the active ingredient is uniformly distributed when the oil-soluble active ingredient is supported inside the particles. In addition, among the oil-soluble active ingredients, there are those of which the potency decreases due to oxidation or modification of the structure when coming into contact with water and those that cause problems such as discoloration and malodor of the formulation.

Hence, it is required to conduct researches on a formulation that is uniformly dispersed in the composition and capable of stabilizing the active ingredient in the solid particles.

SUMMARY OF INVENTION

Technical Problem

In an aspect, an object of the present disclosure is to provide a cosmetic composition in which spherical particles are uniformly dispersed in an aqueous phase and which does not thus cause irritation.

In another aspect, an object of the present disclosure is to prepare particles dispersed in an aqueous phase in a spherical shape and thus to stabilize the active ingredient in the solid particles.

In another aspect, an object of the present disclosure is to support an active ingredient in spherical particles uniformly dispersed in an aqueous phase and thus to recover the skin barrier, to improve wrinkles, or to activate the whitening action.

Solution to Problem

In an aspect, the present disclosure provides a cosmetic composition of dispersion formulation comprising: an aqueous phase as an external phase; and an oil phase consisting of spherical particles dispersed in the aqueous phase, wherein the spherical particles comprise an alcohol having 22 or less carbon atoms and a sucrose-based surfactant.

Advantageous Effects of Invention

In an aspect, the cosmetic composition of dispersion formulation of the present disclosure can minimize irritation when being applied to the skin since spherical particles are uniformly dispersed in an aqueous phase in the cosmetic composition of dispersion formulation. Specifically, the particles are formed in a spherical shape and thus may be evenly distributed in the aqueous phase and evenly applied to the skin surface at the time of the application. In addition, the particles are spherical, thus the active ingredient is uniformly distributed when being supported in the particles, and the stabilization of active ingredient is possible.

BRIEF DESCRIPTION OF DRAWINGS

FIGS. 2 and 3 illustrate the results of transdermal moisture loss measured in a case in which a composition according to Example 4 of the present disclosure and isononyl isononanoate are applied.

DESCRIPTION OF EMBODIMENTS

Definition of Term

Figure 1A:
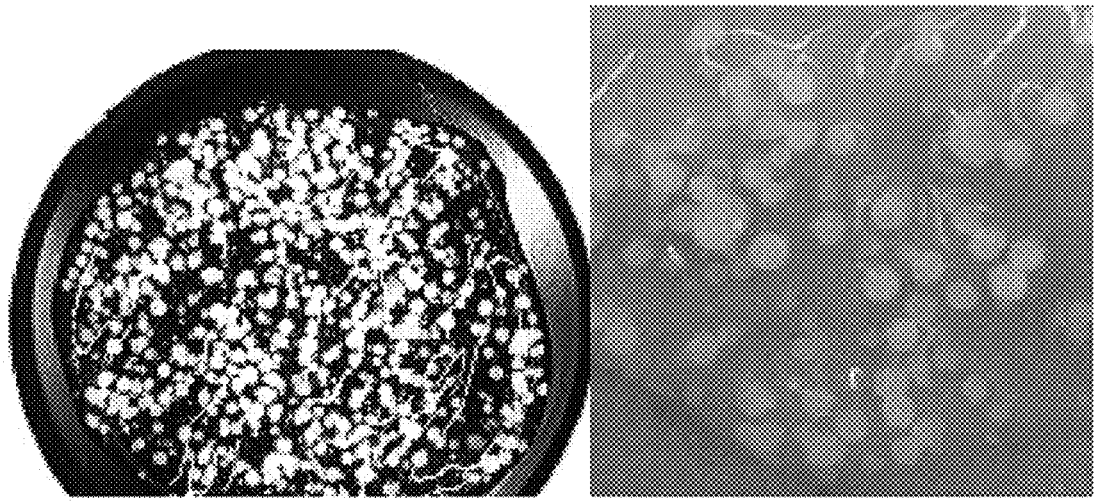
FIG. 1A illustrates a photograph of spherical particles according to Example 1 of the present disclosure.

In the present specification, "sphericity" refers to the extent to which a particle is close to a sphere and is determined by a ratio of the longest length to the shortest length of a particle. In other words, sphericity is expressed as a numerical value closer to 1 as a particle is closer to a sphere. In addition, the spherical particles in the present disclosure are substantially spherical, and to be "substantially spherical" generally means a form which is defined as a volume representing a minimum outer surface area, namely, which is close to a complete sphere. Specifically, to be "substantially spherical" in the present disclosure means that the difference between the large and small diameters is less than 20%, less than 10%, or less than 5% when an arbitrary cross section of the particle is viewed.

In the present specification, "particle diameter" means a diameter of a spherical particle, and "average particle diameter" of spherical particles means an average value of diameters of the respective single particles of spherical particles.

In the present specification, "dispersion formulation" means a formulation in which spherical particles constituting an inner phase are dispersed in an aqueous phase as an external phase.

In the present specification, when it is said that a portion "comprises" a certain constituent, this means that the portion may further comprise other constituents rather than excluding other constituents unless otherwise specifically stated.

DESCRIPTION OF EXEMPLARY EMBODIMENTS

Hereinafter, the present disclosure will be described in detail.

In exemplary embodiments of the present disclosure, the present disclosure relates to a cosmetic composition of dispersion formulation comprising: an aqueous phase as an external phase; and an oil phase consisting of spherical particles dispersed in the aqueous phase, wherein the spherical particles comprise an alcohol having 22 or less carbon atoms and a sucrose-based surfactant.

The spherical particles according to the present disclosure are prepared not in an amorphous form but in a spherical shape unlike the conventional solid particles, thus are aesthetically attractive to the consumers, are uniformly distributed in the cosmetic composition of dispersion formulation, and may be evenly applied together with the aqueous phase as an external phase when being applied to the skin.

The spherical particles do not comprise higher fatty acids or shea butter and the like, but comprise an alcohol having 22 or less carbon atoms, thus exhibit excellent flexibility, do not cause irritation on the skin, and may be uniformly dispersed in the aqueous phase. In a case in which the spherical particles comprise alcohols having more than 22 carbon atoms or higher fatty acids, most of these have a high melting point, and thus the particles are not produced in a spherical shape or are produced as hard particles and may cause irritation on the skin when being applied to the skin.

In addition, fatty acids have an acid as a functional group, but it is considered that the particles have interfacial tension or polarity proper to be formed into a spherical shape when having an alcohol group such as the alcohol of the present disclosure.

In addition, in a case in which shea butter is contained in the inner phase composition, it is difficult to form spherical particles because of the amorphous crystal form of shea butter.

Meanwhile, HLB (hydrophile-lipophile balance) value of surfactant is important for the formation of spherical particles. In the case of the sucrose-based surfactant, the hydrophilic head of the sugar group helps to have an HLB value in an intermediate region. In addition, sugar groups interact with fatty alcohols or fatty ester emollients to help the formation and maintenance of spherical particles.

On the other hand, in the case of containing a surfactant having a long hydrocarbon chain such as arachidyl glucoside or glyceryl stearate in addition to the sucrose-based surfactant, the HLB (hydrophile-lipophile balance) value is low and fine spherical particles are produced and may thus hardly support the active substance.

In an embodiment, the average particle diameter of the spherical particles may be 1 to 5 mm, for example, 1.5 to 4.5 mm, 2 to 4 mm, 2.5 to 3.5 mm, or 2 to 3 mm. In a case in which the average particle diameter is less than 1 mm, the spherical particle size is finer and thus the visual perception effect that the spherical particles melt in and are absorbed into the skin at the time of use may decrease from a visual point of view. Fine particles are aggregated with each other, melt, and dissociated at a high temperature and this is disadvantageous to maintain the stability from the stability point of view. The particles may not have enough space to encapsulate the active ingredient. On the other hand, in a case in which the average particle diameter is more than 5 mm, the particles may cause irritation when being applied to the skin and may not be uniformly dispersed.

In an embodiment, the content of the oil phase may be 5% to 15% by weight, for example, 6% to 14% by weight, 7% to 13% by weight, 8% to 12% by weight, or 9% to 11% by weight based on the total weight of the cosmetic composition. In a case in which the content of the oil phase is less than 5% by weight, the adhesive feel may decrease when the cosmetic composition of dispersion formulation is applied. In a case in which the content is more than 15% by weight, the residual oiliness on the skin may be excessive and this may cause discomfort when the cosmetic composition of dispersion formulation is applied.

In an embodiment, the content of the alcohol having 22 or less carbon atoms may be 1% to 5% by weight based on the total weight of the cosmetic composition, and the content of the sucrose-based surfactant may be 0.1% to 1% by weight based on the total weight of the cosmetic composition.

In a case in which the alcohol content is less than 1% by weight, it is difficult to maintain high-temperature stability. In a case in which the alcohol content is more than 5% by weight, irritation may be caused when the cosmetic composition is applied to the skin.

In a case in which the content of the sucrose-based surfactant is less than 0.1% by weight, the spherical particles may be formed in a large size or the emulsification of the spherical particles itself may be impossible. In a case in which the content is more than 5% by weight, the size of the spherical particles may be extremely small.

In an embodiment, the alcohol having 22 or less carbon atoms may comprise one or more selected from the group consisting of cetyl alcohol, stearyl alcohol, cetearyl alcohol, and behenyl alcohol and may preferably comprise cetearyl alcohol.

In an embodiment, the sucrose-based surfactant may comprise one or more selected from the group consisting of sucrose stearate, sucrose distearate, sucrose cocoate, and acetylated sucrose distearate and may preferably comprise sucrose stearate.

In an embodiment, the spherical particles may further comprise wax comprising one or more selected from the group consisting of myristyl myristate, *Camellia sinensis* leaf extract, jojoba ester, sunflower seed, carnauba wax, candelilla wax, and beeswax; and oil comprising one or more selected from the group consisting of a hydrocarbon-based compound and an ester-based compound, and the oil may preferably comprise squalane.

The content of wax may be 0.5% to 1.5% by weight based on the total weight of the cosmetic composition. In a case in which the content is less than 0.5% by weight, the cohesive force to form spherical particles by the wax may be weak. In a case in which the content is more than 1.5% by weight, the waxes may be aggregated with each other and the stability of the composition may greatly decrease.

The content of the oil may be 5% to 10% by weight based on the total weight of the cosmetic composition. In a case in which the content is less than 5% by weight, the flexibility of formulation may decrease. In a case in which the content is more than 10% by weight, greasiness may be severe when the cosmetic composition is applied.

In an embodiment, the spherical particles may encapsulate an active ingredient. This is the application of solid lipid nanoparticles (SLN) and nanostructured lipid carriers (NLC) to a cosmetic composition from a formulation point of view.

In a case in which the active ingredient is encapsulated in the spherical particles, it is possible to enhance the chemical stability of the active ingredient, is possible not only to increase the skin hydration through the occlusive effect but also to increase the bioavailability of the active ingredient in the skin, and is possible to enhance the physical stability of topical preparations.

In particular, in the case of spherical particles according to the present disclosure, the active ingredient is uniformly distributed in the particles unlike the conventional amorphous particle-dispersed formulation, thus the spherical particles are not oxidized or the structure thereof is not deformed when coming into contact with water, and stability problems such as discoloration and malodor of formulation are not caused.

In an embodiment, the active ingredient may comprise one or more selected from the group consisting of ceramide, Saururus chinensis extract, oil-dispersed adenosine, alpha-misabolol, dioleanolic acid, dipalmitoylhydroxyproline, and a fat-soluble vitamin derivative, but is not limited thereto, and may be preferably ceramide.

In an embodiment, the active ingredient may be contained at 0.5% by weight or less, for example, 0.01% to 0.45% by weight, 0.05% to 0.4% by weight, 0.1% to 0.35% by weight, or 0.15% to 0.3% by weight based on the total weight of the cosmetic composition.

In a case in which the active ingredient is contained at more than 0.5% by weight, ceramide is not dissolved inside the spherical lipid particles but is distributed in a line at the interface at which the ceramide is in contact with the aqueous phase, and the active ingredient serves as a surfactant. When the active ingredient structure (for example, ceramide) is a surfactant structure, the interfacial tension between water (outer phase) and spherical particles (inner phase) may significantly decreases, and it may be difficult to form spherical particles.

In an embodiment, the aqueous phase comprises water as the balance and may further comprise a polyol and a thickener. The polyol serves as a moisturizing agent and may comprise one or more selected from the group consisting of glycerin, propylene glycol, dipropylene glycol, 1,3-butylene glycol, pentylene glycol, and 1,2-hexanediol, and the content thereof may be 10% to 20% by weight based on the total weight of the cosmetic composition. In a case in which the content of the polyol is less than 10% by weight, the moisturizing effect may be slight. In a case in which the content is more than 20% by weight, adverse sensory such as stickiness may be caused.

In an embodiment, the thickener is used to adjust the viscosity of the cosmetics after emulsification of the oil phase and may comprise one or more selected from the group consisting of cellulose, xanthan gum, ammonium acryloyldimethyltaurate/VP copolymer, hydroxyethyl acrylate/sodium acryloyldimethyltaurate copolymer, polyacrylate, polyisobutene, and polysorbate. The content of the thickener may be 0.1% to 0.5% by weight based on the total weight of the cosmetic composition. In a case in which the content of the thickener is less than 0.1% by weight, the dispersibility of the spherical lipid particles may decrease. In a case in which the content is more than 0.5% by weight, stickiness of the composition may be severe.

In an embodiment, the cosmetic composition may be for skin barrier recovery, wrinkle improvement, or whitening enhancement, but the use thereof is not limited thereto.

In other exemplary embodiments of the present disclosure, the present disclosure relates to a method for recovering skin barrier, improving wrinkles, or enhancing whitening comprising administering a cosmetic composition of dispersion formulation comprising: an aqueous phase as an external phase; and an oil phase consisting of spherical particles dispersed in the aqueous phase, wherein the spherical particles comprise an alcohol having 22 or less carbon atoms and a sucrose-based surfactant, to a subject in need thereof in an effective amount.

In other exemplary embodiments of the present disclosure, the present disclosure is a use of a cosmetic composition of dispersion formulation for manufacturing a composition for skin barrier recovery, wrinkle improvement, or whitening enhancement, wherein the cosmetic composition comprises an aqueous phase as an external phase; and an oil phase consisting of spherical particles dispersed in the aqueous phase, wherein the the spherical particles comprise an alcohol having 22 or less carbon atoms and a sucrose-based surfactant.

In other exemplary embodiments of the present disclosure, the present disclosure is a cosmetic composition of dispersion formulation comprising: an aqueous phase as an external phase; and an oil phase consisting of spherical particles dispersed in the aqueous phase, wherein the spherical particles comprise an alcohol having 22 or less carbon atoms and a sucrose-based surfactant, for skin barrier recovery, wrinkle improvement, or whitening enhancement.

EMBODIMENTS

Hereinafter, the present disclosure will be described in more detail with reference to the following Examples. However, the following Examples are provided only for the purpose of illustration in order to help the understanding of the present disclosure, and the gist and scope of the present disclosure are not limited thereto.

EXAMPLES AND COMPARATIVE EXAMPLES

1. Cosmetic Composition of Dispersion Formulation Comprising Oil Phase Consisting of Spherical Particle Cosmetic compositions of Examples 1 to 3 and Comparative Examples 1 to 3 were prepared according to the prescription in Table 1 below.

TABLE 1

| | | Example 1 | Example 2 | Example 3 | Comparative Example 1 | Comparative Example 2 | Comparative Example 3 |
|---|---|---|---|---|---|---|---|
| oil phase | Stearic acid | — | — | — | 2 | — | — |
| | Cetearyl alcohol | 2 | — | — | — | 2 | 2 |
| | Behenyl alcohol | — | 2 | 2 | — | — | — |
| | Shea butter | — | — | — | 0.7 | — | — |
| | Jojoba ester | 0.7 | — | 0.7 | — | 0.7 | 0.7 |
| | Sunflower wax | — | 0.7 | — | — | — | — |
| | MONTANOV 202 | — | — | — | — | — | 0.5 |
| | Sucrose stearate | 0.5 | 0.5 | 0.5 | 0.5 | — | — |
| | Glyceryl stearate | — | — | — | — | 0.5 | — |
| | Squalane | 6.8 | 6.8 | 6.8 | 6.8 | 6.8 | 6.8 |
| Aqueous phase | Purified water | up to 100 | up to 100 | up to 100 | up to 100 | up to 100 | up to 100 |
| | Glycerin | 10 | 10 | 10 | 10 | 10 | 10 |
| | Carbomer | 0.2 | 0.2 | 0.2 | 0.2 | 0.2 | 0.2 |

Figure 1B:
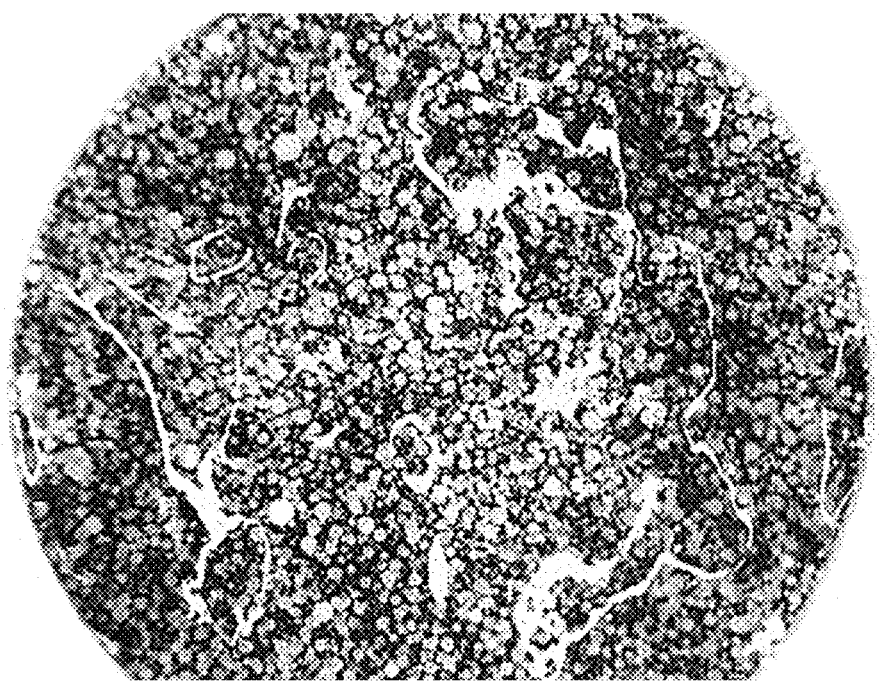
FIG. 1B illustrates a photograph of particles according to Comparative Example 1.
Figure 1C:
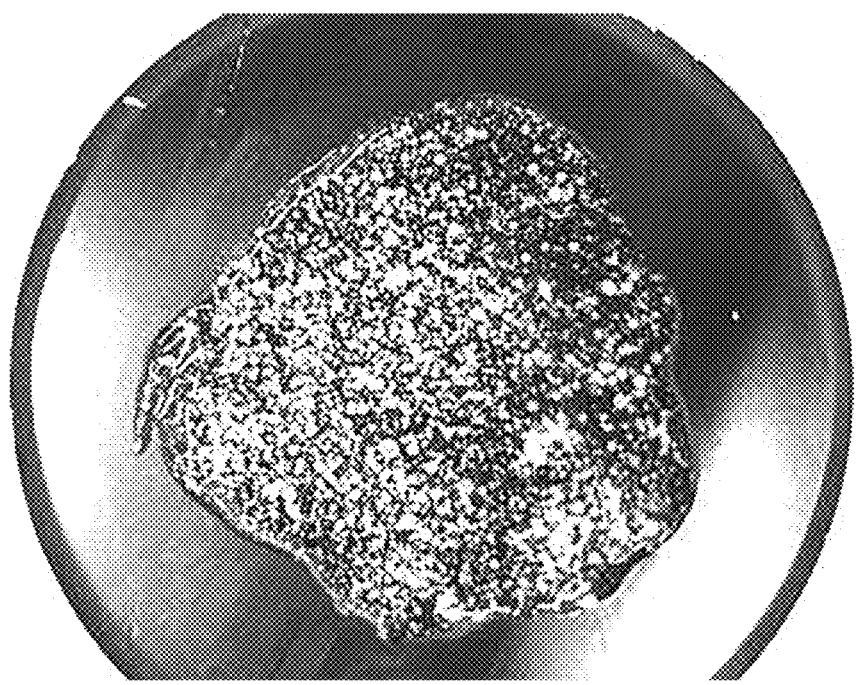
FIG. 1C illustrates a photograph of particles according to Comparative Example 2.

Referring to FIG. 1, in the case of the cosmetic composition according to Example 1, it was found that spherical particles close to a substantially spherical shape were formed and the particles were uniformly dispersed in the formulation. However, in the case of the composition according to Comparative Example 1, the particles were not formed in a spherical shape but were formed in an amorphous form. In the case of the composition according to Comparative Example 2, the particles were formed in a size of 0.3 mm or less and thus were not suitable to be used in a cosmetic composition.

2. Cosmetic Composition of Dispersion Formulation Comprising Oil Phase Having Active Substance Encapsulated Inside Spherical Particle Cosmetic compositions of Example 4 and Comparative Example 4 were prepared according to the prescription in Table 2 below.

TABLE 2

| | Name of raw material | Example 4 | Comparative Example 4 |
|---|---|---|---|
| Oil phase | Cetearyl alcohol | 2 | 2 |
| | Jojoba ester | 0.7 | 0.7 |
| | Sucrose stearate | 0.5 | 0.5 |
| | Ceramide | 0.5 | 1 |
| | Squalane | 6.5 | 6 |
| Aqueous phase | Purified water | up to 100 | up to 100 |
| | Glycerin | 20 | 20 |
| | Ammonium acryloyldimethyl-taurate•VP copolymer | 0.2 | 0.2 |

EXPERIMENTAL EXAMPLES

Experimental Example 1: Stability of Dispersion Formulation

Referring to Table 3 below, all of Examples 1 to 4 were confirmed to exhibit favorable stability when being stored for 4 weeks in thermostats at room temperature (25° C.), refrigeration temperature (4° C.), freezing storage temperature (−20° C.), and a high temperature (45° C.) However, in the case of Comparative Example 1, the particles were agglomerated or aggregated when being stored in a thermostat at a high temperature (45°), and it was indicated that the stability of the formulation was not favorable.

TABLE 3

| | Example 1 | Example 2 | Example 3 | Example 4 | Comparative Example 1 |
|---|---|---|---|---|---|
| Room temperature | Favorable | Favorable | Favorable | Favorable | Favorable |
| Refrigeration temperature | Favorable | Favorable | Favorable | Favorable | Favorable |
| Freezing storage temperature | Favorable | Favorable | Favorable | Favorable | Favorable |
| 45° c. | Favorable | Favorable | Favorable | Favorable | Agglomeration or aggregation of particles |

Experimental Example 2: Measurement of Transdermal Moisture Loss when Applied to Skin Example 4 (solid-liquid formulation) and isononyl isononanoate were applied to the skin, and the skin barrier recovery ability thereof was examined by measuring the transdermal moisture loss.

Figure 3:
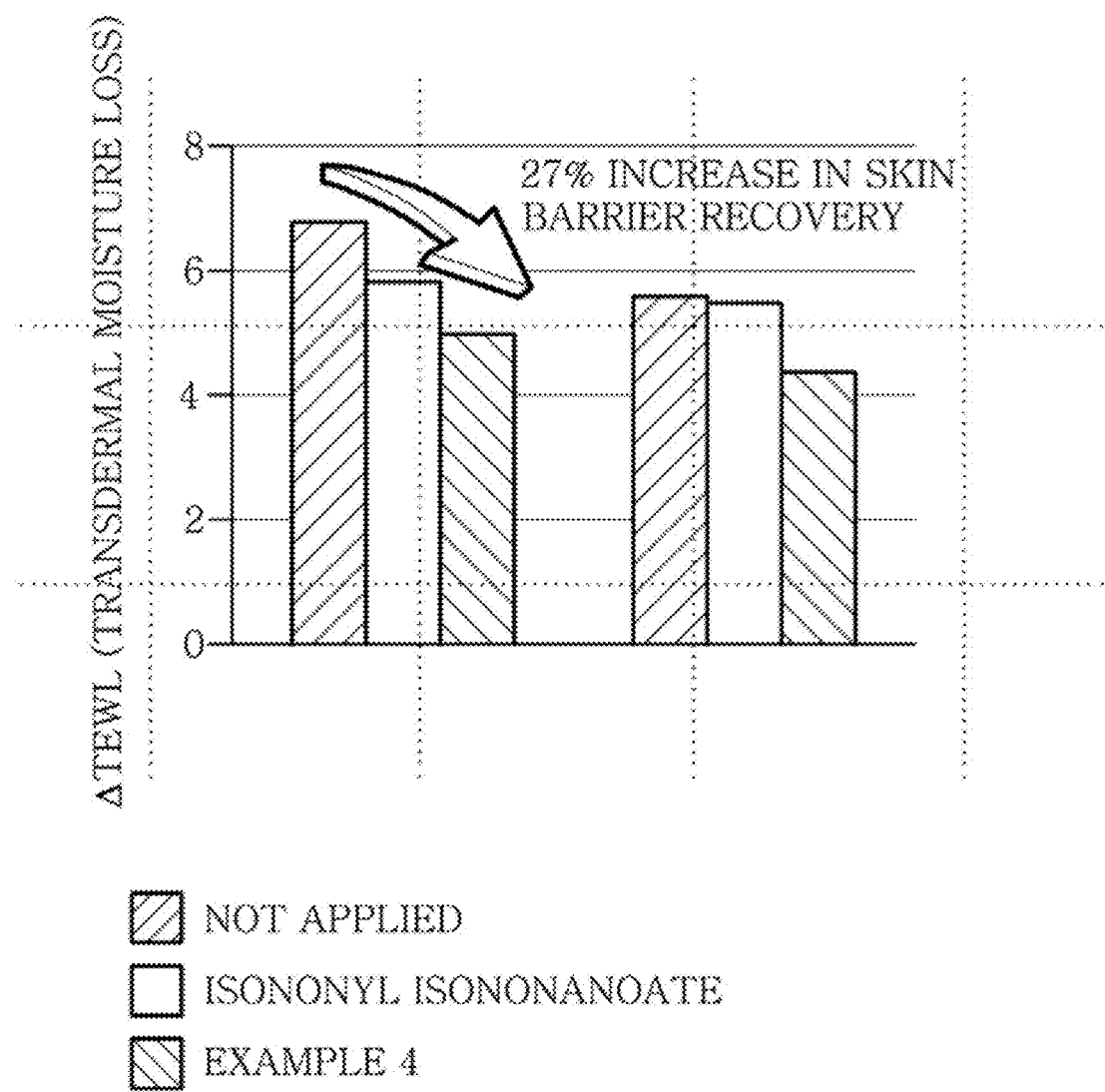

Referring to FIGS. 2 and 3, it was found that the skin barrier recovery ability of Example 4 was higher than that when Example 4 was not applied by approximately 27% when the moisture loss was measured in a state in which an oil formulation (isononyl isononanoate) and Example 4 were not applied to the skin after the skin barrier was damaged and in 3 hours, 8 hours, and 24 hours after the oil formulation (isononyl isononanoate) and Example 4 were applied to the skin.

Experimental Example 3: Sensory Evaluation

Example 4, isononyl isononanoate, and the composition of Comparative Example 4 were applied to the skin to examine the feel of use.

Specifically, a certain amount, about 50 ul, of the sample was dropped on the forearms of 20 women in their twenties to thirties using a pipette and then spread with the index finger 20 times for 10 seconds (2 times/second) to evaluate the feel of use. After 10 seconds, the timer was stopped and the characteristics such as spreadability, hydrating feel, waxy feel, and oily feel were evaluated by scores. At the time point at which the absorption was considered to be almost completed, the skin was pressed by the hand and the hand was detached from the skin to evaluate the residual oiliness and moisturizing feel.

Figure 4A:
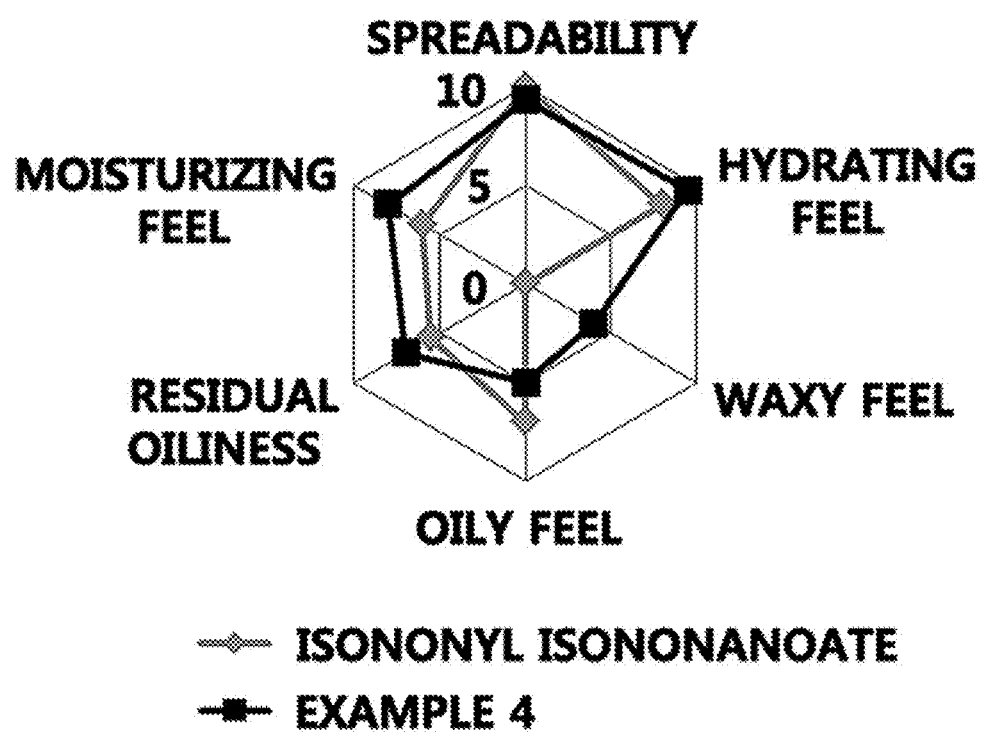
FIG. 4A illustrates the results when feel of use of Example 4 of the present disclosure and feel of use of isononyl isononanoate are compared to each other.
Figure 4B:
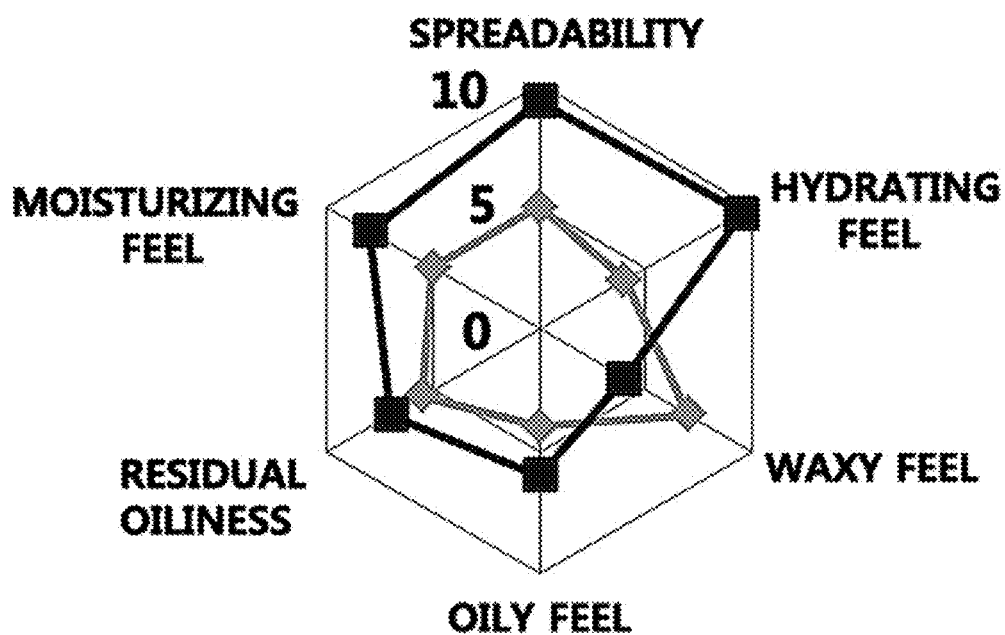
FIG. 4B illustrates the results when feel of use of a composition according to Example 4 of the present disclosure and feel of use of a composition according to Comparative Example 4 are compared to each other.
Figure 5A:
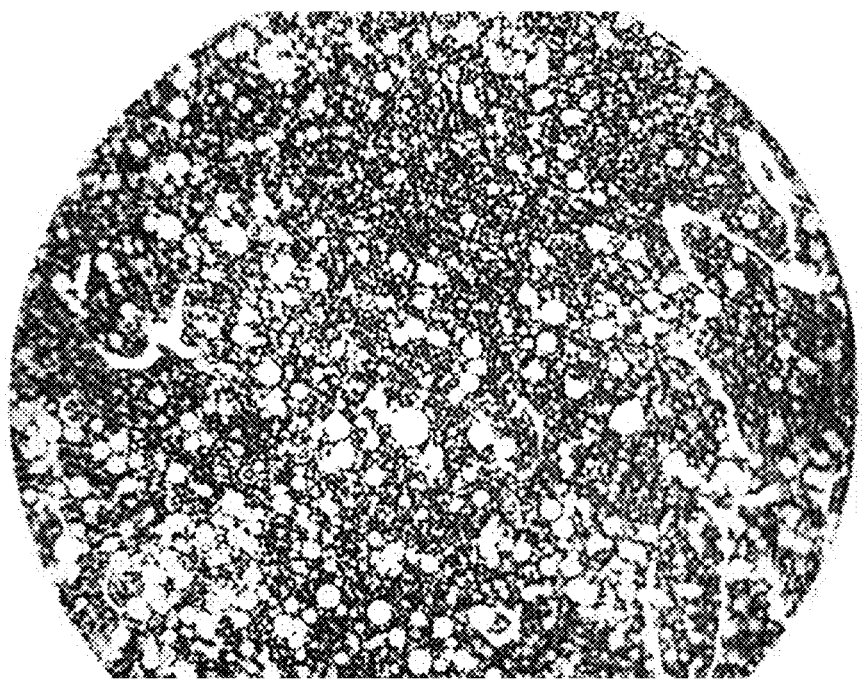
FIG. 5A illustrates a photograph of spherical particles according to Example 4 of the present disclosure.
Figure 5B:
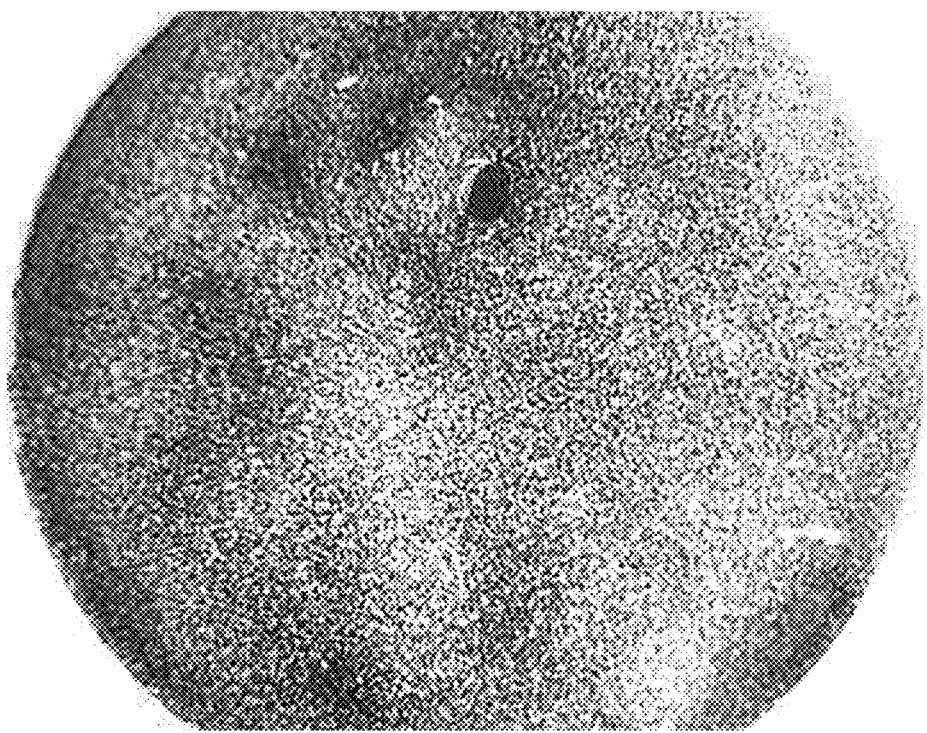
FIG. 5B illustrates a photograph of particles according to Comparative Example 4.

Referring to FIGS. 4A and 4B, as a result, the cosmetic composition according to Example 4 was found to exhibit excellent initial hydrating feel and excellent moisturizing feel after being absorbed. However, it was confirmed that the composition of Comparative Example 4 was significantly inferior in spreadability, moisturizing feel, and hydrating feel. In addition, it was confirmed that isononyl isononanoate was remarkably inferior in waxy feel to the cosmetic composition according to Example 4 of the present disclosure.

The invention claimed is:

1. A cosmetic composition of dispersion formulation comprising:
   an aqueous phase as an external phase; and
   an oil phase consisting of spherical particles dispersed in the aqueous phase,
   wherein the spherical particles comprise an alcohol and a sucrose-based surfactant,
   wherein the alcohol contained in the spherical particles consists of an alcohol selected from the group consisting of stearyl alcohol, cetyl alcohol, cetearyl alcohol, behenyl alcohol, and a combination thereof,
   wherein the sucrose-based surfactant consists of a sucrose-based surfactant selected from the group consisting of sucrose stearate, sucrose distearate, sucrose cocoate, acetylated sucrose distearate, and a combination thereof,
   wherein the spherical particles do not comprise shea butter, and
   wherein the cosmetic composition further comprises an active ingredient that is encapsulated in the spherical particles.

2. The cosmetic composition of dispersion formulation according to claim 1, wherein an average particle diameter of the spherical particles is 1 to 5 mm.

3. The cosmetic composition of dispersion formulation according to claim 1, wherein a content of the oil phase is 5% to 15% by weight based on a total weight of the cosmetic composition.

4. The cosmetic composition of dispersion formulation according to claim 1, wherein
   a content of the alcohol having 22 or less carbon atoms is 1% to 5% by weight based on a total weight of the cosmetic composition, and
   a content of the sucrose-based surfactant is 0.1% to 1% by weight based on a total weight of the cosmetic composition.

5. The cosmetic composition of dispersion formulation according to claim 1, wherein the spherical particles further comprise wax comprising one or more selected from the group consisting of myristyl myristate, *Camellia sinensis* leaf extract, jojoba ester, sunflower seed, carnauba wax, candelilla wax, and beeswax; and oil comprising one or more selected from the group consisting of a hydrocarbon-based compound and an ester-based compound.

6. The cosmetic composition of dispersion formulation according to claim 1, wherein the active ingredient comprises one or more selected from the group consisting of ceramide, Saururus chinensis extract, oil-dispersed adenosine, alpha-misabolol, dioleanolic acid, dipalmitoylhydroxyproline, and a fat-soluble vitamin derivative.

7. The cosmetic composition of dispersion formulation according to claim 1, wherein the active ingredient is contained at 0.5% by weight or less based on a total weight of the cosmetic composition.

8. The cosmetic composition of dispersion formulation according to claim 1, wherein the aqueous phase further comprises a polyol and a thickener.

9. The cosmetic composition of dispersion formulation according to claim 8, wherein
   a content of the polyol is 10% to 25% by weight based on a total weight of the cosmetic composition, and
   a content of the thickener is 0.1% to 0.5% by weight based on a total weight of the cosmetic composition.

10. The cosmetic composition of dispersion formulation according to claim 8, wherein the polyol comprises one or more selected from the group consisting of glycerin, propylene glycol, dipropylene glycol, 1,3-butylene glycol, pentylene glycol, and 1,2-hexanediol.

11. The cosmetic composition of dispersion formulation according to claim 8, wherein the thickener comprises one or more selected from the group consisting of cellulose, xanthan gum, ammonium acryloyldimethyltaurate/VP copolymer, hydroxyethyl acrylate/sodium acryloyldimethyltaurate copolymer, polyacrylate, polyisobutene, and polysorbate.

12. A method for recovering skin barrier, reducing wrinkles, or improving complexion of skin of a subject, comprising administering the cosmetic composition according to claim 1, to skin of the subject in need thereof in an effective amount.

* * * * *